United States Patent
Bontinck

(10) Patent No.: US 8,454,839 B2
(45) Date of Patent: Jun. 4, 2013

(54) METHOD FOR MODIFYING THE PROPERTIES OF A FLUID BY IRRADIATION, AND SYSTEM FOR IMPLEMENTING SAME

(75) Inventor: Pierre-Eloi Bontinck, Lille (FR)

(73) Assignee: Macopharma, Mouvaux (FR)

( * ) Notice: Subject to any disclaimer, the term of this patent is extended or adjusted under 35 U.S.C. 154(b) by 0 days.

(21) Appl. No.: 13/205,439

(22) Filed: Aug. 8, 2011

(65) Prior Publication Data

US 2011/0294157 A1 Dec. 1, 2011

Related U.S. Application Data

(63) Continuation of application No. PCT/FR2010/000098, filed on Feb. 9, 2010.

(30) Foreign Application Priority Data

Feb. 9, 2009 (FR) .................................. 09 00562

(51) Int. Cl.
*C12Q 1/02* (2006.01)
*G21K 5/08* (2006.01)
*C12N 13/00* (2006.01)

(52) U.S. Cl.
USPC ............ 210/748.01; 210/748.11; 210/748.12; 210/143; 210/243; 210/153; 422/186; 422/186.3; 435/29; 435/173.1; 250/428

(58) Field of Classification Search
USPC .................. 210/748.01, 748.11, 748.12, 143, 210/153, 243; 422/186, 186.3; 435/29, 173.1; 250/428
See application file for complete search history.

(56) References Cited

U.S. PATENT DOCUMENTS

| | | | |
|---|---|---|---|
| 6,190,608 B1 * | 2/2001 | Laub et al. ...................... 422/24 |
| 6,951,548 B1 | 10/2005 | Einstein | |
| 2002/0100679 A1 * | 8/2002 | Wedekamp ............... 204/157.15 |
| 2004/0000519 A1 * | 1/2004 | Jiang et al. ..................... 210/634 |
| 2005/0061743 A1 * | 3/2005 | Buttner ......................... 210/646 |
| 2007/0000814 A1 | 1/2007 | Kennedy et al. | |
| 2007/0181509 A1 * | 8/2007 | Araiza et al. .................. 210/748 |

FOREIGN PATENT DOCUMENTS

WO 0020045 A1 4/2000

(Continued)

OTHER PUBLICATIONS

International Search Report for PCT/FR2010/000098, dated May 19, 2010.

(Continued)

*Primary Examiner* — Joseph Drodge
*Assistant Examiner* — Cameron J Allen
(74) *Attorney, Agent, or Firm* — Baker Botts L.L.P.

(57) ABSTRACT

Methods for modifying the physical, chemical and/or biological properties of a fluid by irradiation are provided. In one embodiment, a method comprising supplying a flow of a fluid to an irradiation chamber; focusing the flow of the fluid so as to create at least one fluid layer; and applying radiation to the fluid layer in a defined portion of the irradiation chamber thereby modifying at least one physical, chemical or biological property of the fluid layer is provided. Systems for the implementation of such methods are also provided.

17 Claims, 4 Drawing Sheets

FOREIGN PATENT DOCUMENTS

| | | |
|---|---|---|
| WO | 0238191 A2 | 5/2002 |
| WO | 2004037301 A2 | 5/2004 |
| WO | 2006128047 A2 | 11/2006 |
| WO | 2007076834 A1 | 7/2007 |
| WO | 2007137245 A2 | 11/2007 |
| WO | 2008130977 A2 | 10/2008 |

OTHER PUBLICATIONS

Fuh, C. Bor, et al., "Isolation of Human Blood Cells, Platelets, and Plasma Proteins by Centrifugal SPLITT Fractionation", Biotechnol. Prog. 1995, 11, 14-20.

* cited by examiner

METHOD FOR MODIFYING THE PROPERTIES OF A FLUID BY IRRADIATION, AND SYSTEM FOR IMPLEMENTING SAME

CROSS-REFERENCE TO RELATED APPLICATIONS

This application is a continuation of International Application No. PCT/FR2010/000098, filed Feb. 9, 2010, which claims the benefit of French Application No. 0900562, filed Feb. 9, 2009, the entire disclosures of which are hereby incorporated by reference.

BACKGROUND

The present disclosure generally relates to methods for modifying the physical, chemical and/or biological properties of a fluid by irradiation and also systems for the implementation of such methods.

WO 2007/076834 generally discloses a method for inactivating the pathogens of a platelet concentrate contained in a receptacle by joint agitation and irradiation by means of ultraviolet rays. The agitation permits a statistically uniform irradiation of the platelet concentrate. However, in the case of fluids which are very concentrated or more generally which highly absorb the radiation concerned, such as a concentrate of red blood cells, this method would necessitate either using a very large-sized receptacle, or considerably increasing the duration of the irradiation, making this method impracticable for routine use in blood treatment centers.

WO 2006/128047 generally discloses a system for the irradiation of blood in which the blood is exposed to ultraviolet radiation while it circulates in a plastic tube. However, this flux system does not allow a sufficiently thin layer to be obtained to permit the penetration of the light in a concentrated fluid.

Micro-fluidic devices exist, in particular for sorting, separating and/or detecting particles suspended in a fluid. Such a device is described for example in WO 2008/130977. In this device, the particles are focused and ordered before being separated and analyzed.

SUMMARY

The present disclosure generally relates to methods for modifying the physical, chemical and/or biological properties of a fluid by irradiation and also systems for the implementation of such methods.

The present disclosure applies generally to the irradiation of fluids, such as biological fluids, which are intended to be used in diagnostics, nutrition, therapy, including cellular therapy. In some embodiments, the present disclosure applies more specifically to the reduction of active pathogens present in a fluid, such as blood or blood components, by means of radiation alone, for example ultraviolet C, or by means of association of a photosensitive substance with radiation, for example visible, infrared or ultraviolet light.

In one embodiment, the present disclosure provides a method comprising: supplying a flow of a fluid to an irradiation chamber; focusing the flow of the fluid so as to create at least one fluid layer; and applying radiation to the fluid layer in a defined portion of the irradiation chamber thereby modifying at least one physical, chemical or biological property of the fluid layer.

In another embodiment, the present disclosure provides a method comprising: supplying a flow of a fluid to an irradiation chamber comprising a neutral fluid and a biological fluid; focusing the flow of the fluid so as to create at least two fluid layers in laminar flow, wherein at least one fluid layer comprises the neutral fluid and at least one fluid layer comprises the biological fluid; and applying radiation to the fluid layers in a defined portion of the irradiation chamber.

In yet another embodiment, the present disclosure provides a system comprising: an irradiation chamber comprising at least one inlet for the introduction of a fluid which is to be irradiated in the irradiation chamber and at least one outlet for the withdrawal of the irradiated fluid; an irradiation device; and a focusing device that focuses the fluid which is to be irradiated into at least one fluid layer within a defined portion of the irradiation chamber.

The features and advantages of the present invention will be apparent to those skilled in the art. While numerous changes may be made by those skilled in the art, such changes are within the spirit of the invention.

DRAWINGS

Some specific example embodiments of the disclosure may be understood by referring, in part, to the following description and the accompanying drawings.

Figure 1:
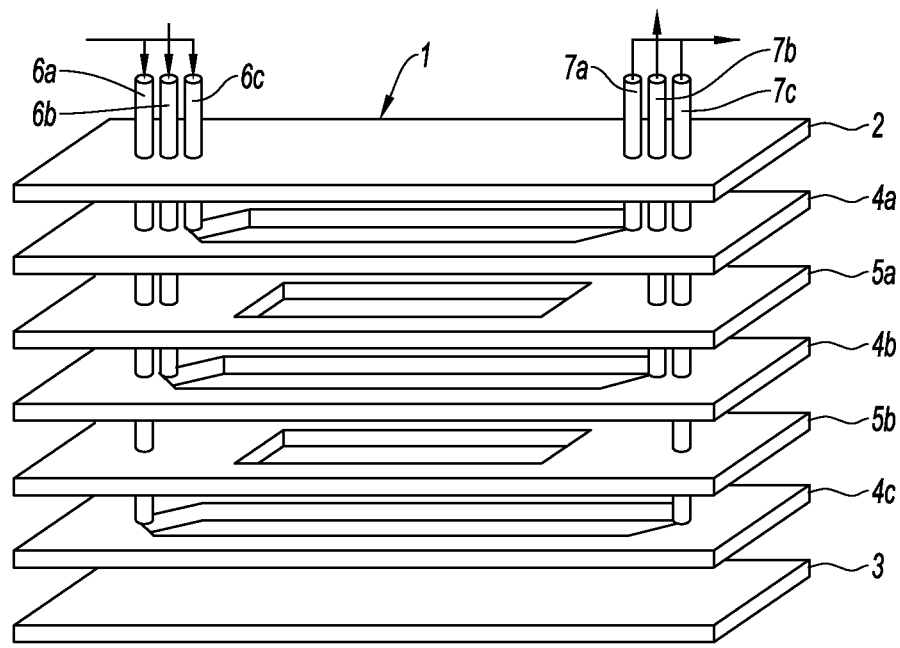
FIG. 1 represents a diagrammatic exploded view of an irradiation chamber according to one embodiment of the present disclosure.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure generally relates to methods for modifying the physical, chemical and/or biological properties of a fluid by irradiation and also systems for the implementation of such methods.

In some embodiments, the fluid which is to be irradiated is, for example, a biological fluid, such as whole blood or a blood component. Examples of suitable blood components may comprise products obtained by apheresis or by centrifuging of whole blood, such as plasma, platelet-rich plasmas, platelet concentrates, cell concentrates, and buffy coat layers. In some embodiments, whole blood or a blood component may be deleukocyted, or depleted in leukocytes, by passage through a deleukocyting filter.

In some embodiments where the fluid to be irradiated is a biological fluid, such as whole blood or a blood component, a photosensitive substance, an additive solution and/or a preservation solution may be added to the fluid. Examples of suitable photosensitive substances may include, but are not limited to, a phenothiazine (methylene blue), a psoralen (methoxypsoralen) or a riboflavin derivative (vitamin B2). A suitable irradiation (visible light or UV) of the fluid comprising the photosensitive substance therefore allows the number of active pathogens therein to be reduced, in particular bacteria and/or viruses. Similarly, an example of a suitable additive solution may include a solution of the SAGM type (saline-adenine-glucose-mannitol), which may be added to a biological fluid, such as a red cell concentrate. Examples of a suitable preservation solution may include a solution of the SSP+ type, marketed by Macopharma, which may be added to, for example, a platelet concentrate.

In some embodiments, the fluid which is irradiated may also comprise a neutral fluid from the point of view of irradiation. A neutral fluid, from the point of view of irradiation, is a fluid which is at least partially permeable to the radiation used. For example, a neutral fluid may include a phosphate buffer, a saline solution, an additive solution, and/or preservation solution of a blood component.

In general, a fluid may be irradiated in accordance with the methods of the present disclosure to reduce the pathogenic contaminations of the fluid. For example, when the fluid is water, a treatment by ultraviolet C irradiation (UVC) allows the number of active bacteria present in the fluid to be eliminated or reduced. In some embodiments, irradiation suitable for use in the present disclosure may include the emission of electromagnetic waves, such as X rays, gamma rays, infrared, visible or ultraviolet rays.

In one specific embodiment, a biological fluid, such as a platelet concentrate or a red cell concentrate may be irradiated with UV radiation having a wavelength in the order of 254 nm, to reduce the number of active pathogens, such as bacteria, viruses and parasites, which may be present in the fluid, and also the leukocytes. In another embodiment, a biological fluid, such as a platelet concentrate, may be irradiated with UVA radiation to reduce its immunogenicity in an alloimmunized patient.

In those embodiments where the fluid to be irradiated is a biological fluid, it is important to apply a sufficient dose of radiation to obtain the desired effect, for example a reduction in active pathogens, while minimizing the damage caused to the elements of the fluid.

According to the methods of the present disclosure, in one embodiment, a flow of a fluid is supplied to an irradiation chamber. In general, the flow rate of the fluid supplied to the irradiation chamber may be controlled. The flow of the fluid to be irradiated is focused so as to create at least one fluid layer within the irradiation chamber and a dose of radiation is applied to the fluid layer so as to modify at least one property of the fluid layer. In some embodiments, the focusing can be carried out by the action of a force field, in particular a hydrodynamic field, allowing thin micrometric fluid layer(s) to be obtained. Thus, even concentrated fluids, such as a red cell concentrate, can be irradiated.

Accordingly, in one embodiment, the methods of the present disclosure may allow for the irradiation of a flow of at least one fluid layer, the thickness of which is substantially constant and defined, thus eliminating the need for a receptacle having a thickness which is as small as the fluid layer.

An irradiation chamber suitable for use in the present disclosure is at least partially permeable to the radiation which is to be applied, i.e. the intensity of at least a part of the incident radiation is transmitted to the interior of the irradiation chamber. In some embodiments, the whole irradiation chamber may be permeable to radiation, while in other embodiments, only a portion of the irradiation chamber may be permeable to radiation. In those embodiments where the radiation to be applied is electromagnetic radiation, the irradiation chamber may comprise any material that is at least partially permeable to electromagnetic radiation. For example, in some embodiments, an irradiation chamber suitable for use in the present disclosure may comprise polycarbonate, quartz, glass, polystyrene, acrylic, polyvinyl chloride, polymethyl methacrylate, or a combination thereof.

In some embodiments, an irradiation chamber may be formed by an assembly of thin films of variable geometries (shape and dimensions). A particular realization of an irradiation chamber according to one specific embodiment is illustrated in FIG. 1. According to this figure, chamber 1 is constituted by thin rectangular films, parallel with each other, such as films 2, 3, 4a, 4b, 4c, 5a, 5b. In some embodiments, films 2, 3, 4a, 4b, 4c, 5a, 5b may comprise polymers and/or metal. In some embodiments, the films may be permeable to radiation.

In some embodiments, the dimensions of a film suitable for use in the present disclosure may have a width of about 1 cm to about 50 cm and a length of about 5 to about 100 cm. The films define a flow path in the form of a channel of micrometric or millimetric thickness. In particular, the thickness of a channel may be about 0.1 mm to about 5 cm and more particularly, between about 0.5 mm and about 0.5 cm. For example, in one embodiment, two parallel films of approximately 3 cm by 15 cm are separated by a distance of approximately 1 mm.

In one embodiment, an irradiation chamber has a planar symmetry characterized by the plane passing through the center of the irradiation chamber, orthogonal to the surface of the films constituting it and to the channel.

In some embodiments, an irradiation chamber may have a thickness that is sufficiently small for the flows inside it to be laminar. A laminar flow is characterized by a low Reynolds number, in particular less than 2320. The Reynolds number is defined by the equation $Re=(\rho V d/\mu)$ in which $\rho$ is the density of the fluid, V is the velocity of the fluid, d is the dimension of the flow and et $\mu$ is the viscosity of the fluid.

If applicable, the superposition of layers of fluid in the irradiation chamber is broadly heterogeneous. If one considers the most severe case, the greatest Reynolds number that can be obtained is linked to great density, speed and dimension, and also to a low viscosity. A large Reynolds number entails a less laminar operating regime.

For example, for a red cell concentrate at 70% hematocrit entering in a chamber between two layers of a neutral fluid, such as sodium chloride at 0.9%, the maximum density for the red cells is in the order of 1.08 g/cm$^3$ and the minimum viscosity in the order of 1 Pa.s for the sodium chloride. With geometric hypotheses, such as the thickness of the channel of the irradiation chamber equal to 1 mm, and a maximum speed at 3.3 cm/s in the center of the irradiation chamber, the calculated Reynolds number is in the order of 0.032; namely a very laminar functioning.

Advantageously, in some embodiments, the width/thickness ratio is high so that the edge effects are small or negligible.

According to another embodiment, a thicker rigid support, which is not depicted in FIG. 1, may be used to shape the irradiation chamber and to compensate for the possible flexibility of the films which are used. This support may avoid the deformation of the irradiation chamber during the flow of the fluids and may also facilitate its handling. The support can be in the form of a frame. The use of one or several frames allows the homogeneity of the thickness of the channel to be ensured over the width and the length of the irradiation chamber.

According to FIG. 1, which represents an exploded view of an irradiation chamber according to one embodiment, the chamber 1 is formed by a superposition of several films. The extreme films 2, 3 form the upper and lower walls of the chamber, and the intermediate films 4a, 4b, 4c, 5a, 5b are in the form of a frame and define the useful zone of the irradiation chamber.

The terms "upper" and "lower" are defined with respect to the irradiation chamber when it is disposed such that the flow of fluid is horizontal. In this configuration, the term "thickness" is defined in the vertical dimension.

In some embodiments, films suitable for use in the present disclosure may comprise a polymeric material and/or metal. Additionally, in certain embodiments, the films may be of the same material as the walls of the irradiation chamber. The films may be assembled in any suitable manner, such as for example, by welding or gluing.

To permit the introduction of a fluid into an irradiation chamber, the chamber comprises at least one inlet 6b for the fluid which is to be irradiated. Similarly, to permit the withdrawal of the irradiated fluid, the irradiation chamber comprises at least one outlet 7b for the irradiated fluid.

According to one embodiment, depicted in FIG. 1, the irradiation chamber has three inlets 6a, 6b, 6c and three outlets 7a, 7b, 7c for the fluids. The fluid which is to be irradiated is forwarded in the chamber 1 through the central inlet 6b, and a neutral fluid from the point of view of irradiation is forwarded through the upper 6c and lower 6a inlets.

The intermediate films 4 and 5 in the form of a frame create a space between the walls. These intermediate frames are of two types: the "splitters" 5a, 5b which separate two fluids before they rejoin each other; and the intermediate frames 4a, 4b, 4c in the opening of which the inlets and outlets of the chamber open out. With the splitters 5a, 5b, these intermediate frames form the useful zone of the chamber, in which the fluids are superposed.

Advantageously, the inlets 6 and outlets 7 open out at different heights in the thickness of the channel, the thickness being in the vertical dimension.

The inlets 6 and outlets 7 may be present in the form of thin ducts, one of the ends of which extends to the exterior of the chamber and is connected to a source of fluid, and the other end of which opens out in the hollow part of a frame 4.

Figure 2:
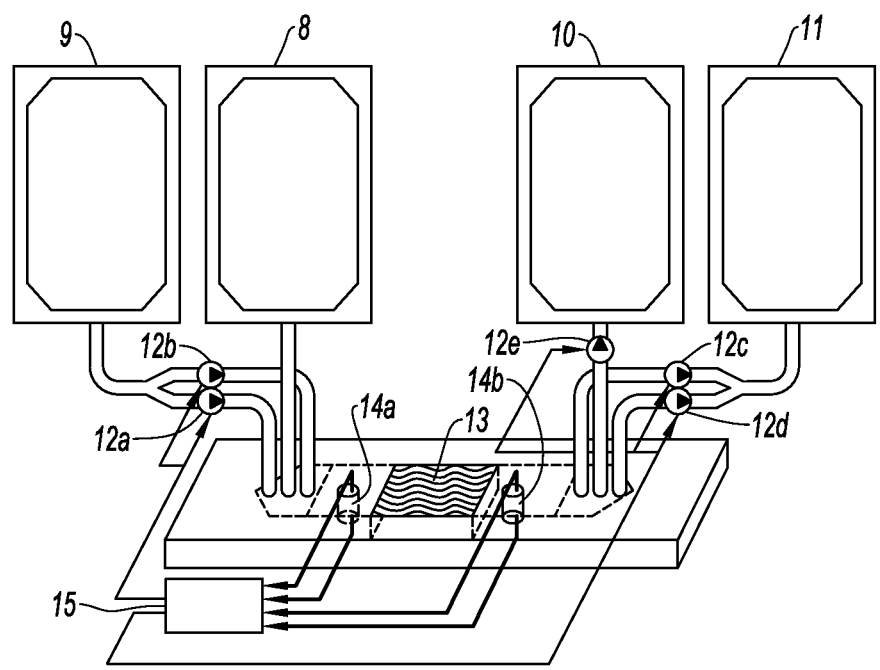
FIG. 2 represents a diagrammatic, perspective view of an irradiation chamber with its peripherals according to one embodiment of the present disclosure.

According to one embodiment, depicted in FIG. 2, the ducts forming the inlets 6 and outlets 7 of the irradiation chamber 1 are connected to flexible tubes of thermoplastic material, which themselves are connected to sources of fluids.

The sources of fluids are constituted by receptacles 8, 9, 10, 11 of the bag type containing the fluids. On the inlet side, the central inlet is in fluidic communication with a bag 8 containing the fluid which is to be irradiated and the upper and lower inlets are in fluidic communication with a shared bag 9 containing a neutral fluid from the point of view of irradiation.

On the outlet side, the central outlet is in fluidic communication with a bag 10 intended to contain the irradiated fluid, and the upper and lower outlets are in fluidic communication with a shared bag 11 intended to collect the neutral fluid which has been irradiated.

In a variant which is not shown, the chamber is of cylindrical shape, as described for example in U.S. Patent Publication No. 2007/0000814, which is incorporated by reference herein. In particular, the chamber is constituted by a solid internal cylinder and a hollow external cylinder which is concentric to the first cylinder, thus creating an annular flow channel between the two cylinders. A splitter at the inlet of the chamber and a splitter at the outlet of the chamber, both in the form of a cylindrical wall, are disposed between the two internal and external cylinders. The chamber is provided with two inlets for two fluids, arranged respectively between the inlet splitter and the external cylinder, and between the inlet splitter and the internal cylinder. In a similar manner, the chamber is further provided with two outlets for the fluids, arranged respectively between the outlet splitter and the external cylinder and between the outlet splitter and the internal cylinder. A cylindrical chamber with three inlets and three outlets is also able to be envisaged.

The Focusing Device

According to the present disclosure, the flow of a fluid which is to be irradiated is focused in a defined portion of the irradiation chamber so as to form at least one fluid layer according to a certain geometry. More particularly, the geometry of the at least one fluid layer, such as the thickness of the fluid layer, is arranged so that a dose of a radiation modifies a physical, chemical and/or biological property of the at least one fluid layer.

In one embodiment, the focusing of the flow of fluid from the central inlet may be realized by the creation of a fluid layer in a channel in the irradiation chamber and more generally by the application of at least one force field suited to displace the particles in a defined portion of the chamber, such as gravitation, centrifugal, magnetic, electrical, acoustic, optic, thermal force and/or lift.

In some embodiments, the focusing of the fluid allows the at least one fluid layer to have a thickness that is smaller than the thickness of the portion of the irradiation chamber in which the fluid which is to be irradiated is focused, i.e. the at least one fluid layer is not in contact with at least one wall or a part of a wall of the irradiation chamber. For example, the at least one fluid layer has a thickness less than 85%, more particularly 50%, of the thickness of the irradiation chamber. This thickness is sufficiently reduced to permit the penetration of a defined radiation over a certain thickness of the fluid layer, in particular over the whole thickness of the layer of fluid to be irradiated.

For example, the thickness of a fluid layer may be reduced such that a UVC radiation emitting at a wavelength of approximately 254 nm penetrates the layer, maintaining a sufficient intensity to produce the desired effect.

In some embodiments, a flow of fluid may be focused so as to create at least two layers, one of which may be a neutral fluid from the point of view of irradiation. The different layers, namely that of the fluid which is to be irradiated and that/those of the neutral fluid, are laminar. Laminar layers are understood to mean layers which slide one over another without the occurrence of turbulences.

More particularly, in an irradiation chamber, a flow of one fluid layer in a first direction according to a first flow rate and a flow of a second fluid layer comprising a neutral fluid in the same direction as the first fluid layer according to a second flow rate is established, so as to form two laminar layers each having a defined thickness in at least a portion of the irradiation chamber.

The two types of fluid, such as a biological fluid and a neutral fluid, may be introduced in the irradiation chamber by the same side. Similarly, they may be introduced separately or simultaneously into the irradiation chamber. However, the two flows of fluids must be present together in the irradiation chamber at a given moment. When they are introduced in the irradiation chamber, the fluids distribute themselves over the thickness of the channel of the chamber.

By varying the flow rates of the fluids, the thickness of the layers of the fluids and their positions in the channel vary as a result. For example, to obtain a thin layer of fluid which is to be irradiated, the flow rate of the fluid which is to be irradiated is less than the flow rate of the neutral fluid. By adjusting the flow rates, a layer of fluid which is to be irradiated having a thickness less than 100 μm can be obtained.

The thickness of the layer of the fluid which is to be irradiated does not therefore depend directly on the thickness of the channel of the irradiation chamber, but is constructed by hydrodynamic manipulation in the interior thereof, by the superposition of the fluid which is to be treated and of layers of a neutral fluid.

In particular, the flow rates of the fluids are comprised between 0.1 ml/min and 200 ml/min, in particular between 1 and 50 ml/min.

To reduce the treatment time of the fluid, several irradiation chambers connected to the same source of fluid which is to be irradiated and one or several sources of neutral fluid may be placed in parallel. Thus, even if the flow rates in one irradiation chamber are low, the plurality of irradiation chambers allows a larger quantity of fluid to be treated than with a single chamber in an acceptable time.

Figure 5:
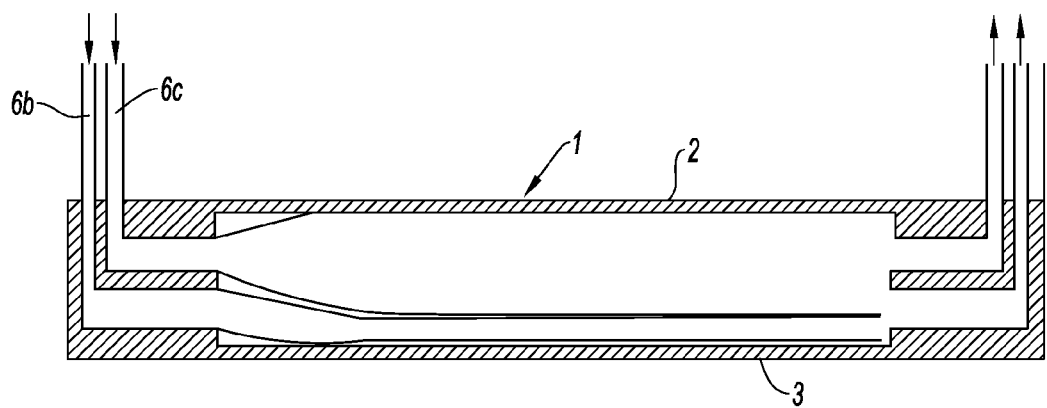
FIG. 5 represents a diagrammatic view, in section, of an irradiation chamber provided with two inlets and two outlets.

In the case where the chamber only comprises two inlets $6b$, $6c$ for the fluid which is to be irradiated and the neutral fluid, as illustrated in FIG. 5, the fluid which is to be irradiated is then focused along one of the walls 3 of the chamber 1.

The use of a chamber with three inlets allows the fluid which is to be irradiated to be prevented from being in contact with the walls of the chamber. For example, in the case of a red cell concentrate, this characteristic allows the shear applied to the fluid to be reduced, and hence allows hemolysis to be limited. It is therefore advantageous, in certain embodiments, to focus the layer of fluid which is to be irradiated between two layers of a neutral fluid. In this case, a flow is established in the irradiation chamber in the same direction as that of the flow of the first fluid, of a second neutral fluid, so as to form three laminar layers, the layer of the fluid which is to be irradiated being disposed between the two other layers of neutral fluids.

The neutral fluids used in the present disclosure may be identical or different. According to FIG. 1, the neutral fluids are introduced through the extreme inlets $6a$, $6c$ of the irradiation chamber, and the fluid which is to be irradiated is introduced through the central inlet $6b$ of the chamber. Thus, the fluid which is to be irradiated is sandwiched between the two layers of neutral fluids, with the latter exerting a protective effect with respect in particular to the walls of the chamber, on the fluid which is to be irradiated.

Figure 3A:
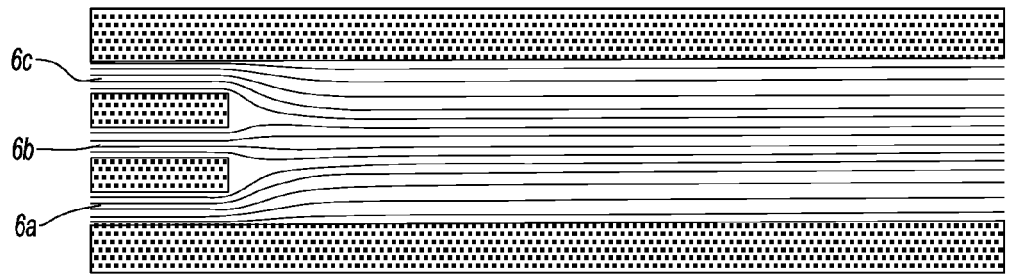
FIG. 3a represents diagrammatically, in a section of an irradiation chamber, close to the inlets, the lines of the current of three fluids having equal flow rates.
Figure 3B:
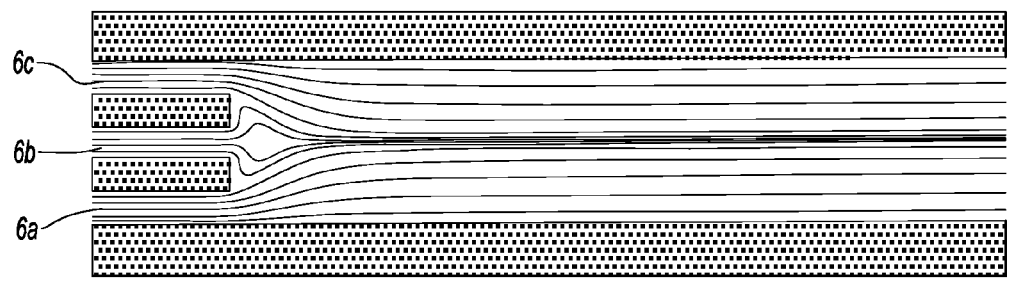
FIG. 3b represents diagrammatically, in a section of an irradiation chamber, close to the inlets, the lines of the current of three fluids, when the flow rate of the central inlet is less than the flow rates of the upper and lower inlets.
Figure 3C:
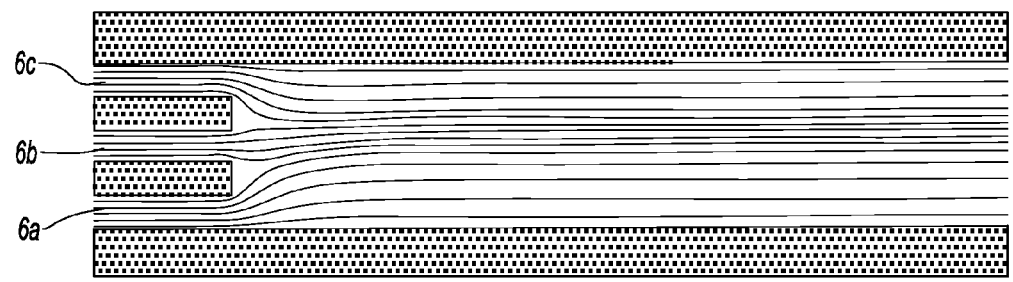
FIG. 3c represents diagrammatically, in a section of an irradiation chamber, close to the inlets, the lines of currents of three fluids, when the flow rate of the lower inlet is greater than the other two.

FIGS. 3a to 3c illustrate three example modes of implementation of the focusing of the fluid with an irradiation chamber having three inlets and three outlets. In FIG. 3a, the flow rates of the fluid which is to be irradiated originating from the central inlet $6b$ and of the neutral fluids originating from the extreme inlets $6a$ and $6c$ are equal. The flow of the fluid which is to be irradiated is focused on the center of the irradiation chamber 1.

In FIG. 3b, the flow rates of the neutral fluids originating from the upper $6c$ and lower $6a$ inlets of an irradiation chamber are identical and greater than the flow rate of the fluid which is to be irradiated, penetrating through the central inlet $6b$ of the irradiation chamber. The fluid which is to be irradiated is focused on the center of the thickness of the irradiation chamber, with a reduced thickness with respect to the thickness of the flow of FIG. 3a.

In FIG. 3c, the flow rate of the neutral fluid originating from the lower inlet $6a$ is greater than the flow rate of the neutral fluid originating from the upper inlet $6c$. The layer of fluid which is to be irradiated is therefore displaced towards the top of the irradiation chamber.

According to an embodiment, the supply of the flow of fluid is realized by a fluid circulation device intended to establish the flows of fluid in the irradiation chamber, comprising a fluid circulating means, such as pump, for example a peristaltic pump, and a means for controlling the flow rates, for example a pump regulator.

According to FIG. 2, the fluid circulating device comprises a set of five pumps $12a$ to $12e$.

A first pump $12a$ and a second pump $12b$ are disposed on one of the tubes connected to the source of neutral fluid 9, respectively. These two pumps entrain the neutral fluid in the irradiation chamber.

A third pump $12c$ and a fourth pump $12d$ are disposed on each of the tubes connected to the bag 11 which is intended to collect the irradiated neutral fluid. The fifth pump $12e$ is disposed on the tube connected to the bag 10 which is intended to collect the irradiated fluid.

It will be noted that in this implementation, it is not necessary to pump the fluid which is to be irradiated in the irradiation chamber. In fact, the irradiation chamber is rigid and the hydrostatic pressure equilibrium draws the fluid which is to be irradiated when the imposed flow rates are such that Qa+Qc+Qd+Qe+Qf<0, wherein Qa is the flow rate of the upper fluid inlet, Qb is the flow rate of the central fluid inlet, Qc is the flow rate of the lower fluid inlet, Qd is the flow rate of the upper fluid outlet, Qe is the flow rate of the central fluid outlet, and Qf is the flow rate of the lower fluid outlet.

The flow rate signs are such that the positive sign indicates that a fluid is pushed in the chamber and the negative sign indicates that a fluid is drawn from the chamber.

The control and the regulation of the flows of the fluids in the irradiation chamber allow the fluid which is to be irradiated to be focused in a defined portion of the chamber, on a defined thickness and at a defined speed.

For example, in the case of a chamber with three inlets, this is highlighted by the relation : $Qa/Q=3\ Wa^2-2\ Wa^3$, with Wa being the ratio of thickness of the layer of fluid issued from the upper inlet, i.e. its thickness divided by the thickness of the chamber and $Q=Qa+Qb+Qc=-Qd-Qe-Qf$. This relation can be easily demonstrated with the following hypotheses: the chamber is much wider than it is thick, the speed profile is therefore parabolic according to thickness, and the fluids are uniform and Newtonian.

It is therefore established that the thickness of the layer of fluid only depends on the ratio of inlet flow rates. Likewise, one has $Qc/Q=3\ Wc^2-2Wc^3$ for the lower inlet. On the other hand, the thickness of the layer issued from the central inlet follows another equation, because it has no contact with a wall. One has $Qb/Q=1-3Wa^2-3Wc^3+2Wa^2+2Wc^2$, which can be verified by $Qb/Q=1-Qa/Q-Qc/Q$. Thus, starting from the desired thicknesses, the necessary flow rates may be calculated. These thicknesses are fixed as a function of the fluid which is to be irradiated.

The Irradiation Device

According to the present disclosure, after the formation of at least one fluid layer, a dose of radiation is applied to the fluid layer(s). The dose is determined, at least in part, based on the speed of the fluid layer(s) in the irradiation chamber, the thickness of the fluid layer(s), and the size of the irradiation window. Other parameters that may be taken into consideration are the permeability to radiation of the irradiation chamber, of the neutral fluid(s) and of the fluid which is to be irradiated and the power of the radiation source.

In general, the dose should be sufficient to cause the desired effect on the fluid layer which is to be irradiated, and in particular to modify the physical, chemical and/or biological properties of the fluid layer. The physical, chemical and/or biological properties are, for example, the loss or reduction of biological activity of the pathogens which may be present in the fluid, such as replication capabilities, or the loss of immunogenicity of the platelets or of the red cells.

As would be recognized by a person of skill in the art with the benefit of this disclosure, the dose of radiation received by the fluid layer determines the efficacy of the treatment. Accordingly, a suitable dose for inactivating pathogens should be one that is sufficient to inactivate the pathogens. However, it must not be too great, so as not to damage the biological properties of the fluid which is to be treated, if applicable.

In one embodiment, the methods of the present disclosure comprise determining the speed and/or thickness of the flow of the fluid layer which is to be irradiated in the portion of the chamber in which the fluid is focused. In some embodiments, this determination may be carried out prior to irradiation. In another embodiment, the opacity of the fluid which is to be irradiated is determined continuously in the frequency range or ranges of the irradiation which is to be carried out. These steps may allow the dose of radiation to be controlled and, if applicable, adjust the flow of fluid and/or the geometry of the fluid layer.

The dose of radiation may be applied by any suitable irradiation device. Suitable types of irradiation devices are those devices that are capable of generating radiation, such as devices capable of generating electromagnetic radiation. In one embodiment, an irradiation device is suited to deliver a defined dose of radiation as a function of the speed and the thickness of the fluid layer which is to be irradiated, and which is sufficient to modify the desired properties of the fluid which is to be irradiated.

Figure 6:
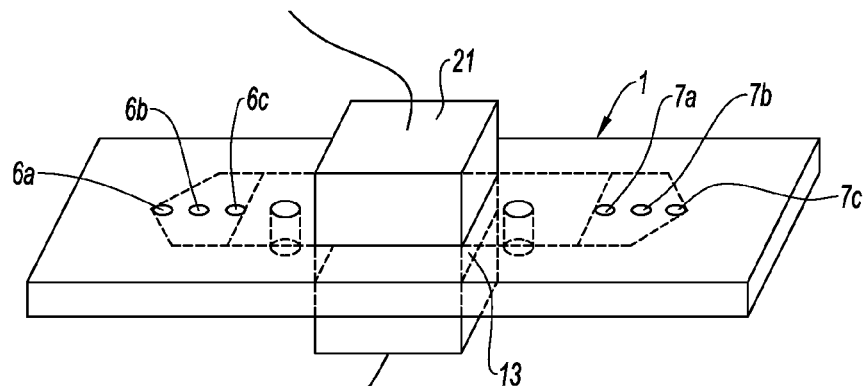
FIG. 6 represents a diagrammatic view of an irradiation chamber with three inlets and three outlets and also an irradiation device.

For example and according to FIG. 6, the irradiation device 21 is constituted by a light source such as a fluorescent lamp, electroluminescent diodes, discharge lamps or filament lamps. The irradiation device can also comprise other elements such as a reflector, a filter or an optical lens.

The irradiation device may be disposed above, below or on either side of the irradiation chamber so as to irradiate transversely the flow of fluid which is to be irradiated.

In particular and in relation to FIG. 2, a defined portion 13 of the useful zone of the irradiation chamber is dedicated to the passage of the radiation which is to be applied to the fluid layer(s). Portions can also serve to place one or several non-contact sensors 14a, 14b so as to carry out different measurements upstream and downstream of the zone which is to be irradiated. In particular, in certain embodiments, it may be desirable to measure the thickness, the speed and/or the opacity of the fluid layer which is to be irradiated. In certain embodiments, sensors may be used to monitor that the device for circulating the fluids and/or the irradiation device are working properly.

Accordingly, in one embodiment, a method of the present disclosure may further comprise regulating the flow rates of the fluids as a function of the desired thickness of the fluid which is to be irradiated and of the thickness which is ascertained. Likewise, a method of the present disclosure may further comprise regulating the intensity of the radiation as a function of the ascertained thickness of fluid which is to be irradiated.

Figure 4:
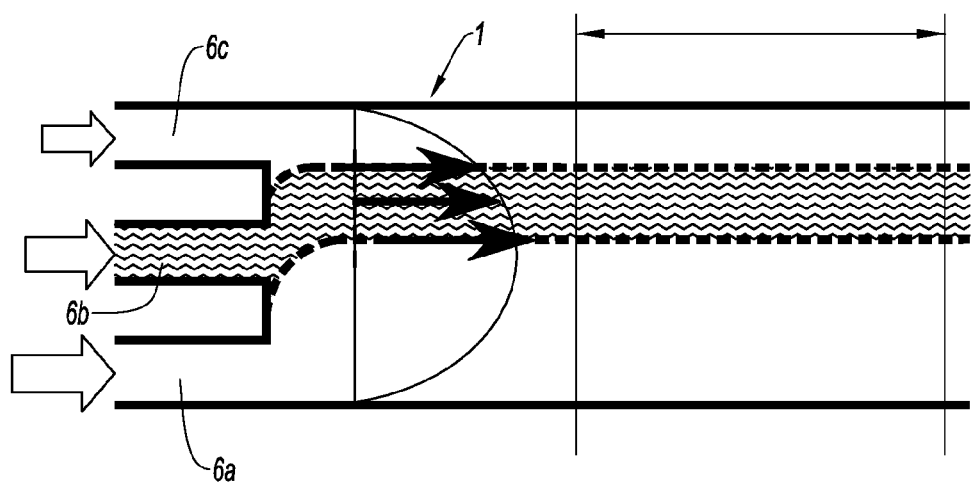
FIG. 4 represents a diagrammatic view, in section, of a portion of an irradiation chamber in which the flow is laminar and the profile of the speeds is parabolic.

In the channel of the irradiation chamber, the fluid which is to be irradiated has a parabolic speed profile, as illustrated in FIG. 4. Thus, in the case of a cell concentrate, the cells in the center of the fluid layer will have a slightly greater speed than that of the cells placed at the extremes of the fluid layer.

This particular profile allows it to be ensured, under certain conditions, that each cell is irradiated since, even if at a given moment, two cells are in the same irradiation axis, at the moment afterwards they will be staggered since they do not have exactly the same speed in the channel. For this, the fluid must be strictly in one half or the other of the thickness of the chamber, or the irradiation is carried out through the top and the bottom of the chamber.

According to another embodiment, the present disclosure provides a system for implementing a method for modifying the physical, chemical and/or biological properties of a fluid by irradiation with a dose of a radiation, comprising: an irradiation chamber 1 comprising at least one inlet 6b for the introduction of the fluid which is to be irradiated in the irradiation chamber, and an outlet 7b for the withdrawal of the irradiated fluid; a device for irradiation of the fluid which is suited to deliver a dose of radiation; and a device for focusing a flow of the fluid in a defined portion of the irradiation chamber 1, according to a geometry arranged so that the dose modifies the physical, chemical and/or biological properties of the fluid which is to be irradiated.

In one embodiment, the device for focusing the flow comprises a fluid circulation device 12a, 12b, 12c, 12d, 12e of fluid, intended to establish the flows of fluid in the irradiation chamber.

In some embodiments, the system may further comprise at least one sensor suited to determine the speed and the thickness of the fluid layer(s) in the irradiation chamber. In addition, the system may further comprise at least one sensor allowing the continuous determining of the opacity of the fluid which is to be irradiated in the frequency range or ranges of the irradiation which is to be carried out.

In particular, the system may further comprise a control device comprising a servo means suited to regulating the flow rates as a function of the desired thickness of the layer of fluid which is to be irradiated and of the ascertained thickness and/or a servo means suited to regulate the intensity of the radiation as a function of the ascertained thickness of the layer of the fluid which is to be irradiated.

In FIG. 2, the control device is, for example, a microcontroller 15.

The System with Several Modules (Mixing and Sorting)

According to a particular embodiment, the irradiation chamber is disposed in series with other treatment chambers similar to those described for the irradiation chamber. In particular, the treatment chambers permit a laminar flow of the fluids.

For example, when the fluid which is to be irradiated is a biological fluid, such as a blood component with the addition of a photosensitive substance, a first chamber intended to mix proportionally the photosensitive substance and the blood component is disposed upstream of the irradiation chamber. The mixing is carried out by varying the flow rates of the blood component and of a solution containing the photosensitive substance.

Figure 7:
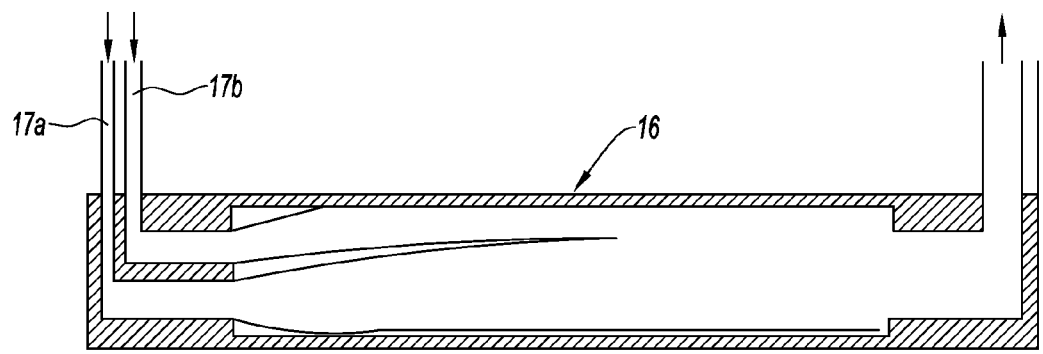
FIG. 7 represents a diagrammatic view, in section, of a chamber intended for the mixing of two fluids.

In particular, according to FIG. 7, the chamber 16 intended for the mixing is provided with at least two inlets 17a, 17b for each of the fluids which are to be mixed, respectively. For example, the first fluid is the biological fluid, and the second fluid is a solution containing a photosensitive substance such as a phenothiazine. By application of a force field transverse to the flow of the fluids, and by adjusting the flow rates of the two fluids which are to be mixed in the mixing chamber, the flow rate ratio between the two fluids is determined. This ratio is, in particular, also a function of the geometry of the chamber, of the coefficients of diffusion of the fluids and of the desired dosage.

In another example, the chamber upstream of the irradiation chamber is a chamber intended for the separation of fluid, so as to separate the fluid which is to be irradiated. In particular, the separation chamber allows the separation of the different types of blood cells (C. Bor Fuh et J. C. Giddings, 1995).

In another example, downstream of the irradiation chamber, a second separation chamber can be disposed, intended to separate the treated cells by illumination of the pathogens and/or of the residual pathogens.

In another example, the irradiation modifies inter alia the properties of the particles with respect to a given force field. The separation chamber downstream therefore makes use of this modification of characteristic to separate the particles.

Figure 8:
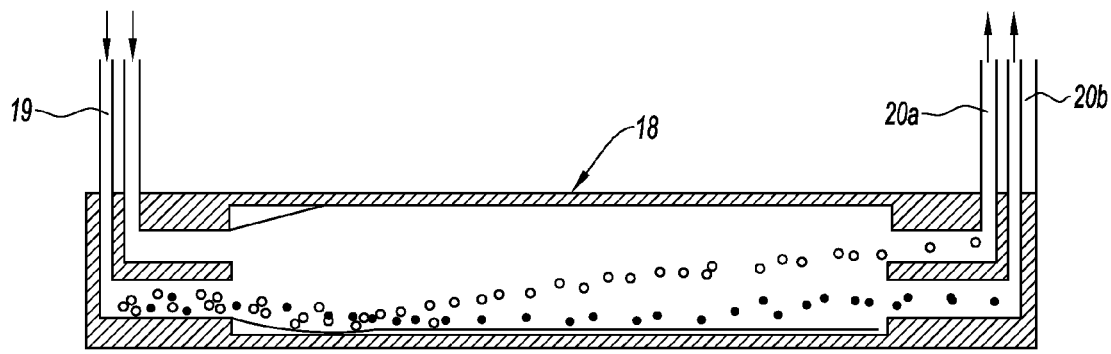
FIG. 8 represents a diagrammatic view, in section, of a chamber intended for the separation of two types of particles contained in a fluid by coupling with a separation force, such as gravity, a magnetic, electrical, ultrasonic field, centrifugal force or else the lift forces of the particles close to the wall.

According to FIG. 8, a chamber 18 intended for separation comprises at least one inlet 19 for the composite fluid which is to be separated, and two outlets 20a, 20b for the separated elements. By applying a force field perpendicular to the plane of the flow of the fluids, the particles comprised in the composite fluid migrate according to their size and their coefficient of diffusion, so as to separate them.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   supplying a flow of a fluid to an irradiation chamber;
   focusing the flow of the fluid by applying a hydrodynamic force to the fluid so as to create at least one fluid layer, wherein the hydrodynamic force is applied by at least one other fluid layer, wherein the at least one other fluid layer comprises a neutral fluid and the fluid layers are in laminar flow; and
   applying radiation to the at least one fluid layer in a defined portion of the irradiation chamber thereby modifying at least one physical, chemical or biological property of the fluid layer.

2. The method of claim 1 wherein the at least one fluid layer has a thickness that is less than the thickness of the defined portion in the irradiation chamber.

3. The method of claim 1 wherein the at least one fluid layer has a thickness that is less than 100 μm.

4. The method of claim 1 wherein focusing the flow of the fluid so as to create the at least one fluid layer further comprises applying one or more forces to the flow of the fluid selected from the group consisting of: centrifugal, acoustic, magnetic, optical, electrical, thermal and lift.

5. The method of claim 1 wherein a flow rate of the at least one other fluid layer comprising the neutral fluid is greater than a flow rate of the at least one fluid layer.

6. The method of claim 1 wherein the hydrodynamic force is applied by at least two other fluid layers, wherein the at least two other fluid layers comprise a neutral fluid, the at least one fluid layer is disposed between the at least two other fluid layers comprising the neutral fluid, and the fluid layers are in laminar flow.

7. The method of claim 1 wherein the defined portion of the irradiation chamber is a channel having a thickness between about 0.1 millimeters to about 5 centimeters.

8. The method of claim 1 further comprising:
   determining at least one of the following properties: the opacity of at least one of the fluid layers, the speed of the flow of at least one of the fluid layers, the thickness of at least one of the fluid layers, and the dose of radiation applied to the fluid layers; and
   adjusting the dose of radiation applied to the fluid layers based at least in part on this determination.

9. The method of claim 1 wherein the radiation comprises ultraviolet radiation.

10. The method of claim 1 wherein the at least one fluid layer comprises a biological fluid.

11. The method of claim 1 wherein the at least one fluid layer comprises a biological fluid selected from the group consisting of: whole blood and a blood component.

12. The method of claim 1 wherein the at least one fluid layer comprises a biological fluid and one or more selected from the group consisting of: a photosensitive substance, an additive solution and a preservation solution.

13. The method of claim 1 wherein modifying at least one physical, chemical or biological property of the at least one fluid layer comprises reducing the number or activity of pathogens in the at least one fluid layer.

14. A method comprising:
   supplying a flow of a fluid to an irradiation chamber, wherein the fluid comprises a biological fluid;
   focusing the flow of the fluid by applying a hydrodynamic force to the fluid, wherein the hydrodynamic force is applied by at least one fluid layer comprising a neutral fluid, so as to create at least two fluid layers in laminar flow, wherein at least one fluid layer comprises the neutral fluid and at least one fluid layer comprises the biological fluid; and applying radiation to the fluid layers in a defined portion of the irradiation chamber.

15. The method of claim 14 wherein focusing the flow of the fluid so as to create at least two fluid layers further comprises applying one or more forces to the flow of the fluid selected from the group consisting of: centrifugal, acoustic, magnetic, optical, electrical, thermal and lift.

16. The method of claim 14 wherein focusing the flow of the fluid creates at least three fluid layers in laminar flow, wherein at least two of the fluid layers comprise the neutral fluid, at least one fluid layer comprises the biological fluid, and wherein the at least one fluid layer comprising the biological fluid is disposed between the at least two fluid layers comprising the neutral fluid.

17. A method comprising:

supplying a flow of a fluid to an irradiation chamber;

focusing the flow of the fluid by applying a hydrodynamic force to the fluid so as to create at least one fluid layer;

applying radiation to at least one fluid layer in a defined portion of the irradiation chamber thereby modifying at least one physical, chemical or biological property of the fluid layer;

determining at least one of the following properties of the fluid layer to be irradiated: opacity of at least one fluid layer, speed of the flow of at least one fluid layer, thickness of at least one fluid layer, and dose of radiation applied to at least one fluid layer; and adjusting the dose of radiation applied to at least one fluid layer based at least in part on this determination.

* * * * *